(12) United States Patent
Lin

(10) Patent No.: US 8,836,936 B2
(45) Date of Patent: Sep. 16, 2014

(54) INSPECTING DEVICE FOR DETECTING APPEARANCE OF DEBRIS ON A SURFACE OF A GLASS SUBSTRATE, INSPECTING APPARATUS AND METHOD FOR CONDUCTING INSPECTION

(71) Applicant: Shenzhen China Star Optoelectronics Technology Co., Ltd., Shenzhen (CN)

(72) Inventor: Yung-Yu Lin, Shenzhen (CN)

(73) Assignee: Shenzhen China Star Optoelectronics Technology Co., Ltd, Shenzhen, Guangdong (CN)

( * ) Notice: Subject to any disclaimer, the term of this patent is extended or adjusted under 35 U.S.C. 154(b) by 0 days.

(21) Appl. No.: 13/818,982

(22) PCT Filed: Feb. 19, 2013

(86) PCT No.: PCT/CN2013/071664
§ 371 (c)(1),
(2), (4) Date: Feb. 25, 2013

(65) Prior Publication Data
US 2014/0218725 A1 Aug. 7, 2014

(30) Foreign Application Priority Data
Feb. 5, 2013 (CN) .......................... 2013 1 0046334

(51) Int. Cl.
*G01N 21/00* (2006.01)
*G01N 21/94* (2006.01)
*B60S 1/08* (2006.01)

(52) U.S. Cl.
CPC ............... *G01N 21/94* (2013.01); *B60S 1/0822* (2013.01)
USPC ..................................................... 356/239.8

(58) Field of Classification Search
CPC .. G01N 21/94; G01N 21/9501; B60S 1/0822; B60S 1/0837; B60S 1/0844
USPC ............... 356/364, 239.8; 430/5; 219/121.67; 250/459.1
See application file for complete search history.

(56) References Cited

U.S. PATENT DOCUMENTS

| | | | |
|---|---|---|---|
| 2005/0041243 A1* | 2/2005 | Choo et al. ................. | 356/239.1 |
| 2009/0220864 A1* | 9/2009 | Tanabe ............................. | 430/5 |
| 2012/0126142 A1* | 5/2012 | Matsui et al. ............... | 250/459.1 |
| 2012/0132628 A1* | 5/2012 | Kosmowski et al. ..... | 219/121.67 |
| 2012/0282311 A1* | 11/2012 | Schmid et al. ................ | 424/401 |

* cited by examiner

*Primary Examiner* — Tarifur Chowdhury
*Assistant Examiner* — MD Rahman
(74) *Attorney, Agent, or Firm* — Andrew C. Cheng

(57) ABSTRACT

The present invention discloses an inspecting device for detecting whether there is an appearance of debris on a surface of a glass substrate, including a laser unit, a platform, and an image sensor unit. The surface of the platform is coated with a light-absorbing material so as to absorb laser beams penetrating through the glass substrate to prevent the image sensor unit from receiving the reflected laser beam from the underside of the glass substrate. Besides, the present invention discloses an inspecting apparatus for detecting whether there is an appearance of debris on a surface of a glass substrate, using the inspecting device given above, and a method for conducting inspection. The inspecting device features a simplified configuration; the method is easy to operate; and the device can effectively prevent the background interference from the underside of glass substrates when determining whether there is an appearance of debris on top surfaces of glass substrates. The device prevents mistakes in detecting glass substrates; and the device improves the accuracy rate of inspection.

5 Claims, 3 Drawing Sheets

INSPECTING DEVICE FOR DETECTING APPEARANCE OF DEBRIS ON A SURFACE OF A GLASS SUBSTRATE, INSPECTING APPARATUS AND METHOD FOR CONDUCTING INSPECTION

FIELD OF THE INVENTION

The present invention relates to a technical field of a production of glass substrate, and more particularly to an inspecting device for detecting whether there is an appearance of debris on a surface of a glass substrate, its method, and an inspecting apparatus for determining whether there is debris appeared on a surface of a glass substrate.

BACKGROUND OF THE INVENTION

In production of glass substrate, surfaces of glass substrates are generally scanned by a laser scanner to determine whether there is debris thereon or not. Normally, a laser scanner for raw glass substrate is used, and a platform thereof is mounted with a plurality of pins to support the glass substrate, such as shown in FIG. 1. FIG. 1 is a structural and illustration view of a prior art inspecting device for detecting whether there is an appearance of debris on a surface of a glass substrate and which is the main configuration of the laser scanner for raw glass substrate for determining whether there is debris appeared on a surface of a glass substrate. A platform 12 is neatly mounted with a plurality of pins 15 for supporting a glass substrate 14. The glass substrate 14 is transferred by rollers, and sometimes traces are marked down on the underside of the glass substrate 14 during displacement. When an existing laser scanner is used to conduct a scanning over a top surface of the glass substrate 14 to determine whether there is an appearance of debris, a laser unit 11 will project laser beams toward the top surface of the glass substrate 14, and the laser beam will further reach to the underside of the glass substrate after refraction. Then, a charge-coupled device (CCD) image sensor 13 will be used to collect the reflected laser beam. However, not only the reflected beam from the top surface of the glass substrate 14 will be collected, but also the reflected laser beam from the underside will be collected. The traces 19 marked on the underside of the glass substrate 14 could be mistakenly interpreted that there is debris 18 appeared on the top surface of the glass substrate 14, such as shown in FIG. 2. FIG. 2 is a scanning result after the inspecting device of FIG. 1 completes its scanning over the glass substrate. It can readily see that it not only demonstrates there is an appearance of debris 18 on the top surface, but also demonstrates the appearance of the traces 19 from the underside of the glass substrate 14. This scanning result will cause the laser scanner to mistakenly interpret that the glass substrate 14 is defective and a cleaning process, or reworking is needed. In worst scenario, the glass substrate 14 could mistakenly be trashed away. The mass production will be negatively affected. As a result, there is a necessity to improve the existing laser scanner for raw glass substrate so as to effectively eliminate the unwanted interference caused by the reflected laser beam from the underside of the glass substrate.

SUMMARY OF THE INVENTION

It is an object of the present invention to provide an inspecting device for detecting whether there is an appearance of debris on a surface of a glass substrate, which can readily resolve the prior art problems that are easily spoilt by the background interference from the underside of glass substrates when determining whether top surfaces of glass substrates are clean or not.

In order to resolve the prior art issue, the present invention introduces a technical solution by providing an inspecting device for detecting whether there is an appearance of debris on a surface of a glass substrate, and includes a laser unit projecting laser beams to the surface of the glass substrate. A platform is provided to carry the glass substrate, and includes a surface coated with a light-absorbing material so as to absorb laser beams penetrating through the glass substrate. An image sensor unit is provided to collect reflected laser beams from the surface of the glass substrate to inspect the surface of the glass substrate.

Wherein the light-absorbing material is a coating of the silicon dioxide.

Wherein a lens for redirecting reflected laser beams from the surface of the glass substrate to the image sensor unit is included.

Wherein a mirror for directing reflected laser beams from the laser unit to the glass substrate is included.

Wherein the laser unit is perpendicular to the glass substrate.

In order to resolve the prior art issue, the present invention introduces a technical solution by providing an inspecting apparatus for detecting whether there is an appearance of debris on a surface of a glass substrate, including anyone of the inspecting devices for detecting whether there is an appearance of debris on a surface of a glass substrate described above.

In order to resolve the prior art issue, the present invention introduces a technical solution by providing a method for conducting inspection, and includes the following steps. a) The step of directing laser beams to the surface of the glass substrate. b) The step of absorbing laser beams penetrating through the glass substrate. c) The step of collecting reflected laser beams from the surface of the glass substrate to inspect the surface of the glass substrate. Wherein reflected laser beams from the surface of the glass substrate are redirected to the image sensor unit by the lens. Wherein laser beams directing to the glass substrate are directed to the glass substrate by the mirror.

The present invention can be concluded with the following advantages. As compared to the existing technology, the inspecting device for detecting whether there is an appearance of debris on a surface of a glass substrate and the method for conducting inspection prevent the image sensor unit from receiving the reflected laser beam from the underside of the glass substrate by coating the surface of the platform with light-absorbing material for absorbing laser beams penetrating through the glass substrate. The inspecting device features a simplified configuration; the method is easy to operate; and the device can effectively prevent the background interference from the underside of glass substrates when determining whether there is an appearance of debris on top surfaces of glass substrates. The device prevents mistakes in detecting glass substrates; and the device improves the accuracy rate of inspection.

BRIEF DESCRIPTION OF DRAWINGS

In order to give a better and thorough understanding to the whole and other intended purposes, features and advantages of the technical solution of the present invention, detailed description will be given with respect to preferred embodiments provided and illustrated here below in accompanied drawings. Apparently, with the spirit of the embodiments disclosed, persons in the skilled in the art can readily come out with other modifications as well as improvements without undue experiment. In addition, other drawings can be readily achieved based on the disclosed drawings. Wherein.

DETAILED DESCRIPTION OF PREFERRED EMBODIMENTS

Detailed description will be given with respect to preferred embodiments provided and illustrated here below in accompanied drawings, and a better and thorough understanding to the whole and other intended purposes, features and advantages of the technical solution of the present invention will be given. Apparently, the embodiments described just disclosed the spirit of the present invention, not all. Any modifications or improvements made according to the disclosure and drawings of the present invention, is considered encompassed in the scope of protection defined by the clams of the present invention.

Figure 1:
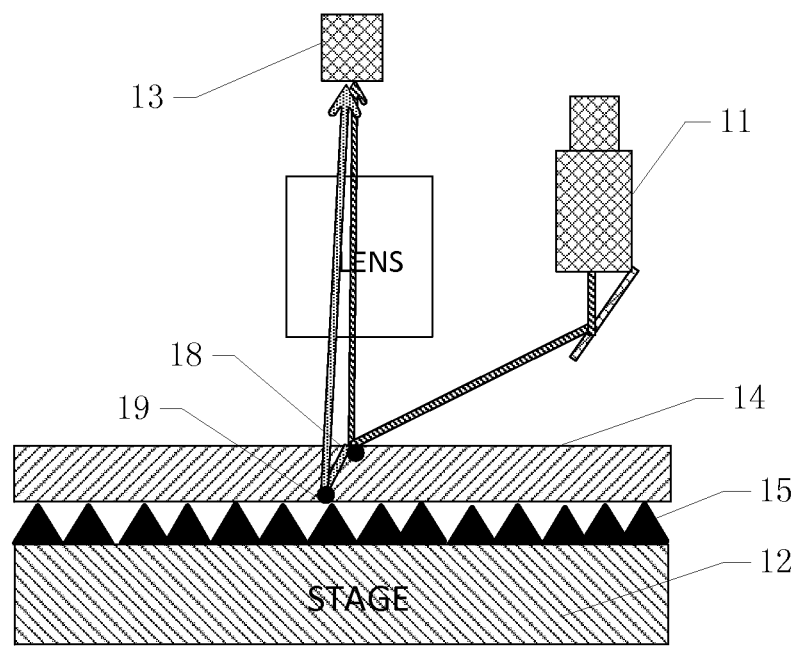
FIG. 1 is a structural and illustration view of a prior art inspecting device for detecting whether there is an appearance of debris on a surface of a glass substrate.
Figure 2:
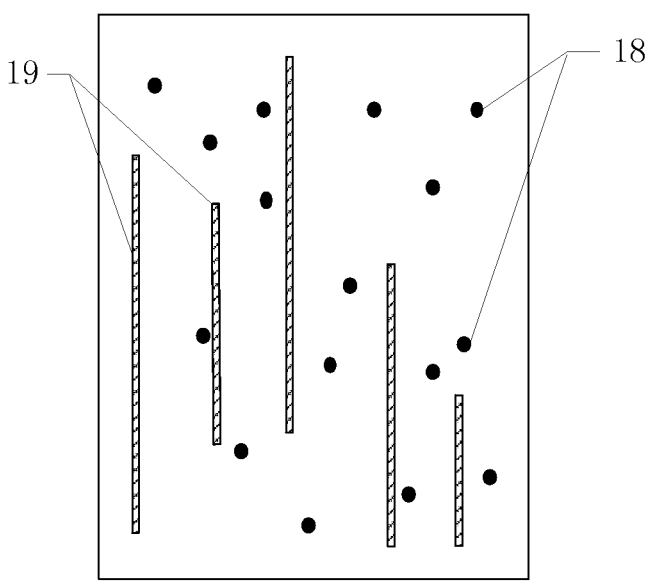
FIG. 2 is a scanning result after the inspecting device of FIG. 1 completes its scanning over the glass substrate.
Figure 3:
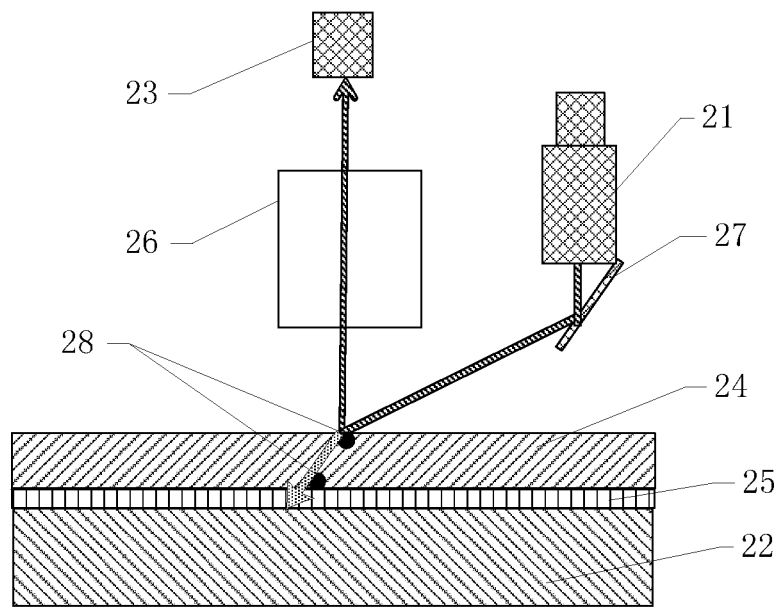
FIG. 3 is a structural and illustration view of an inspecting device made in accordance with the present invention for detecting whether there is an appearance of debris on a surface of a glass substrate.
Figure 4:
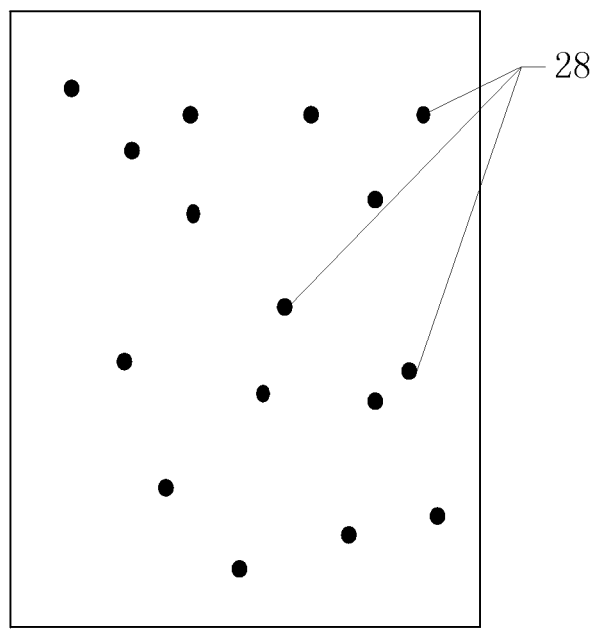
FIG. 4 is a scanning result after the inspecting device of FIG. 3 completes its scanning over the glass substrate.

Referring to FIG. 3, which is a structural and illustration view of an inspecting device made in accordance with the present invention for detecting whether there is an appearance of debris on a surface of a glass substrate. If there is an appearance of debris on a surface of a glass substrate, then the manufacturing process will be negatively affected. For example, the microcircuit formed on the top surface of the glass substrate through the vacuum evaporation deposition will be negatively affected by debris appeared on the top surface of the glass substrate. As a result, there is a necessity to detect whether there is an appearance of debris on a surface of a glass substrate. As shown in FIG. 3, the inspecting device made in accordance with the present invention can be used to detect whether is a foreign object appeared on a top surface of a glass substrate 24. The inspecting device includes a laser unit 21, a platform 22, and an image sensor unit 23. The laser unit 21 is used to project laser beams to the surface of the glass substrate 24. The laser unit 21 can be a laser emitter, and laser beams emitted will be projected outward. The laser unit 21 is positioned above the platform 22. The platform 22 is used to carry the glass substrate 24. The platform 22 is provided with a smooth top surface on which the glass substrate 24 is closely seated without any gap there between. When the glass substrate 24 is undergone an inspection, the platform 22 is driven steadily to pass through under the laser unit 21 and the image sensor unit 23. The top surface of the platform 22 facing the glass substrate 24 is coated with a layer of light-absorbing material 25 so as to absorb the laser beam hitting thereon. Accordingly, the laser beam hitting to the top surface, i.e. the light absorbing material will reflect such that the debris 28 appeared on the underside of the glass substrate 24 will not create a refraction which can be mistakenly interpreted as an appearance of the debris 28 on the top surface of the glass substrate 24. As shown in FIG. 4. FIG. 4 which is a scanning result after the inspecting device of FIG. 3 completes its scanning over the glass substrate; and only shows debris 28 appeared on the top surface of the glass substrate 24 without showing the debris 28 appeared on the underside.

The light-absorbing material used herewith means when a light beam hits onto the light-absorbing material, no penetration will be encountered except being illuminated. On the other hand, no mapping or illuminated spot will be generated as well. The light-absorbing material used in accordance with the present invention is a coating of the silicon dioxide. The coating material comprises the silicon dioxide as aggregate; industrial alcohol as diluter for the base materials; shellac as adhesive for the base materials; bentonite as thickeners; and rare earth oxides as adjuvant.

The composition of the laser light-absorbing coating material in accordance with function are mainly the aggregate, the base materials, including the diluter and the adhesive, the thickeners, and the adjuvant. The aggregate is a vital ingredient of the coating material system, and is also the main part of the composition of the light-absorbing effective ingredients. In addition, except the higher absorption rate to laser beams, the coating of the silicon dioxide will be liquefied under exposure of laser beams, while resumes to a solidified film once it is cooled down. On the other hand, the silicon dioxide as coating the aggregate features a wide resource, a lowered price, and no sputtering after being heated. As a result, the silicon dioxide is selected as the aggregate of the light-absorbing material in accordance with the present invention. The base materials serve as the diluter and the adhesive. The thickeners could be used to adjust the performance of spraying process, so as to meet the requirements of forming a film of coating after it is mixed with the base materials. The light-absorbing coating material should feature a readily pre-coating process, a smooth resulted surface, a uniform thickness, an excellent lamination between coatings and the base materials, no environmental pollution, and a lowered price. In order to achieve an excellent lamination between coatings and the base materials, the coating material should have a certain viscosity. As a result, the industrial alcohol is selected as the diluter; and the shellac is selected as the adhesive for absorbing materials. In order to meet the requirements of a readily coating process and stability under storage, the thickeners should be added to the absorbing materials. According to the present invention, the bentonite is selected as the thickeners. The rare earth improves the surface activity of coating particles; and improves the absorption of light. Therefore, the rare earth is selected as adjuvant for coating materials. During the observation of the test of the light-absorbing materials, it is found that coating materials, made by directly mixing all ingredients without any further processing, not only a poor spraying process will be encountered, but also will have loose coatings, uneven thickness, and poor formation. As a result, a grinding process is selected to process coating materials for improving formation and light-absorbing performance.

An image sensor unit 23 is used to collect reflected laser beams from the surface of the glass substrate 24 to conduct an inspection of the surface of the glass substrate 24. The reflected laser beams from the surface of the glass substrate 24 are projected from the laser unit 21. The image sensor unit 23 receives and analyzes laser beams for determining whether there is an appearance of the debris 28, and then identifies the position of the debris 28 with images. According to the present invention, the image sensor unit 23 includes a CCD camera with an optical imaging system, and the CCD camera is equipped with an optical lens with high resolution 26 and a filter (not shown in Figure). The image sensor unit 23 converts images identified by the optical imaging system of the CCD camera into electrical signal. The CCD camera should be sensitive to the light source no matter whether it is a black-and-white or color camera, which means that if the light source is red light, then the CCD camera which is sensitive to infrared light will be selected. The images of the glass substrate 24 are acquired from the CCD camera, and the electrical signal would be transmitted to an information processor of the image sensor unit 23. According to the present invention, the information processor is a computer equipped with a display and pertinent software.

The inspecting device for detecting whether there is an appearance of debris on a surface of a glass substrate further includes a lens 26 for redirecting reflected laser beams from the surface of the glass substrate 24 to the image sensor unit 23. The inspecting device for detecting whether there is an appearance of debris on a surface of a glass substrate further includes a mirror 27 for directing reflected laser beams from the laser unit 21 to the glass substrate 24. The mirror 27 is positioned below the laser unit 21, and tilted so that laser beams from the laser unit 21 could reach to the glass substrate 24, which is positioned just below the image sensor unit 23 and the lens 26. The laser unit 21 is perpendicular to the glass substrate 24, and laser beams from the laser unit 21 is perpendicular to the glass substrate 24 before reaching to the mirror 27.

Figure 5:
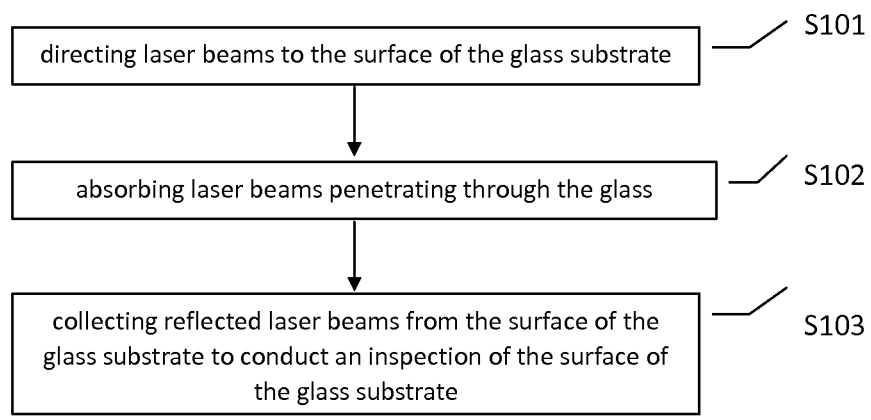
FIG. 5 is a flow-chart diagram illustrating the steps of performing the inspecting device made in accordance with the present invention.

FIG. 5 is a flow-chart diagram illustrating the steps of performing the inspecting device made in accordance with the present invention. As shown in FIG. 5, the method for conducting inspection of the debris 28 on a surface of a glass substrate includes the followings steps.

Step S101, directing laser beams to the surface of the glass substrate 24.

The laser unit 21 projects laser beams to the surface of the glass substrate 24, and reflected laser beams from the laser unit 21 are directed to the glass substrate 24 by the mirror 27.

Step S102, absorbing laser beams penetrating through the glass substrate 24.

Because the glass substrate 24 is transparent, laser beams from the laser unit 21 reach to the top surface of the glass substrate 24, and will further reach to the underside of the glass substrate 24 after refraction. Then, laser beams will be absorbed by the light-absorbing material 25 coated on the surface of the platform 22 facing the glass substrate 24. By this arrangement, laser beams from reflecting from the debris 28 on underside of the glass substrate 24 would not be reflected and then transmitted to the CCD camera of the image sensor unit 23, and thereby the debris 28 on underside would not be mistakenly detected.

Step S103, collecting reflected laser beams from the surface of the glass substrate 24 to conduct an inspection of the surface of the glass substrate 24.

Reflected laser beams from the laser unit 21 are redirected to the image sensor unit 23 by the lens 26 after reaching to the surface of the glass substrate 24. The image sensor unit 23 processes the received images; analyzes for determining whether there is an appearance of the debris 28; and determines the position of the debris 28.

The present invention further provides an inspecting apparatus with the inspecting device described above, and further includes an anti-vibration device and a cleaning device. The anti-vibration device prevents vibration of the platform, and the cleaning device is used to clean and remove the debris on the glass substrate.

In summary, persons in the skilled in the art can readily understand. The present invention discloses an inspecting device for detecting whether there is an appearance of debris on a surface of a glass substrate and the method for conducting inspection to prevent the image sensor unit from receiving the reflected laser beam from the underside of the glass substrate by coating the surface of the platform with light-absorbing material for absorbing laser beams penetrating through the glass substrate. The inspecting device features a simplified configuration; the method is easy to operate; and the device can accurately determine whether there is an appearance of debris instead of the background interference from the underside of glass substrates when determining whether there is an appearance of debris on top surfaces of glass substrates. The device prevents cleaning processes, reworking, or scrapping during production of glass substrate; and the device improves the accuracy rate of inspection.

Embodiments of the present invention have been described, but not intending to impose any unduly constraint to the appended claims. Any modification of equivalent structure or equivalent process made according to the disclosure and drawings of the present invention, or any application thereof, directly or indirectly, to other related fields of technique, is considered encompassed in the scope of protection defined by the clams of the present invention.

The invention claimed is:

1. A method for conducting inspection on a surface of a glass substrate, including the steps of:
    providing a platform having a working surface coated with a light-absorbing material;
    disposing a laser unit arranged above the working surface and capable of projecting an inclined laser beam to scan the upper surface of the platform;
    disposing an image sensor located above the working surface of the platform and distant to the laser unit, and capable of collecting an image thereunder;
    disposing a glass substrate having top and bottom surfaces onto the working surface of the platform and with the bottom surface in close contact with the working surface of the platform;
    projecting an inclined laser beam toward the top surface of the glass substrate wherein part of the inclined laser beam penetrated through a thickness of the glass substrate and emits the bottom surface of the glass substrate is absorbed by the light-absorbing material of the working surface of the platform to refrain a refraction therefrom so as to eliminate an reflected image of the bottom surface of the glass substrate, while part of the inclined laser beam is reflected by the top surface of the glass substrate;
    collecting image of the top surface illuminated by the inclined laser beam by the image sensor to determine whether there is an foreign object appeared on the top surface of the glass substrate; and
    advancing the platform to complete the scan of the top surface of the glass substrate.

2. The method as recited in claim 1, wherein the laser unit is arranged with a mirror in which laser beam projected from the laser unit is obliquely redirected toward the working surface of the platform.

3. The method as recited in claim 1, wherein a lens is arranged between the image sensor and the working surface of the platform.

4. The method as recited in claim 1, wherein the light-absorbing material is a coating of the silicon dioxide.

5. The method as recited in claim 1, wherein the light-absorbing material comprises the silicon dioxide as aggregate, industrial alcohol as diluter for the base materials, shellac as adhesive for the base materials, bentonite as thickeners, and rare earth oxides as adjuvant.

* * * * *